Dec. 10, 1957 E. S. BOERNER Plant Pat. 1,666
CHRYSANTHEMUM PLANT
Filed April 12, 1957
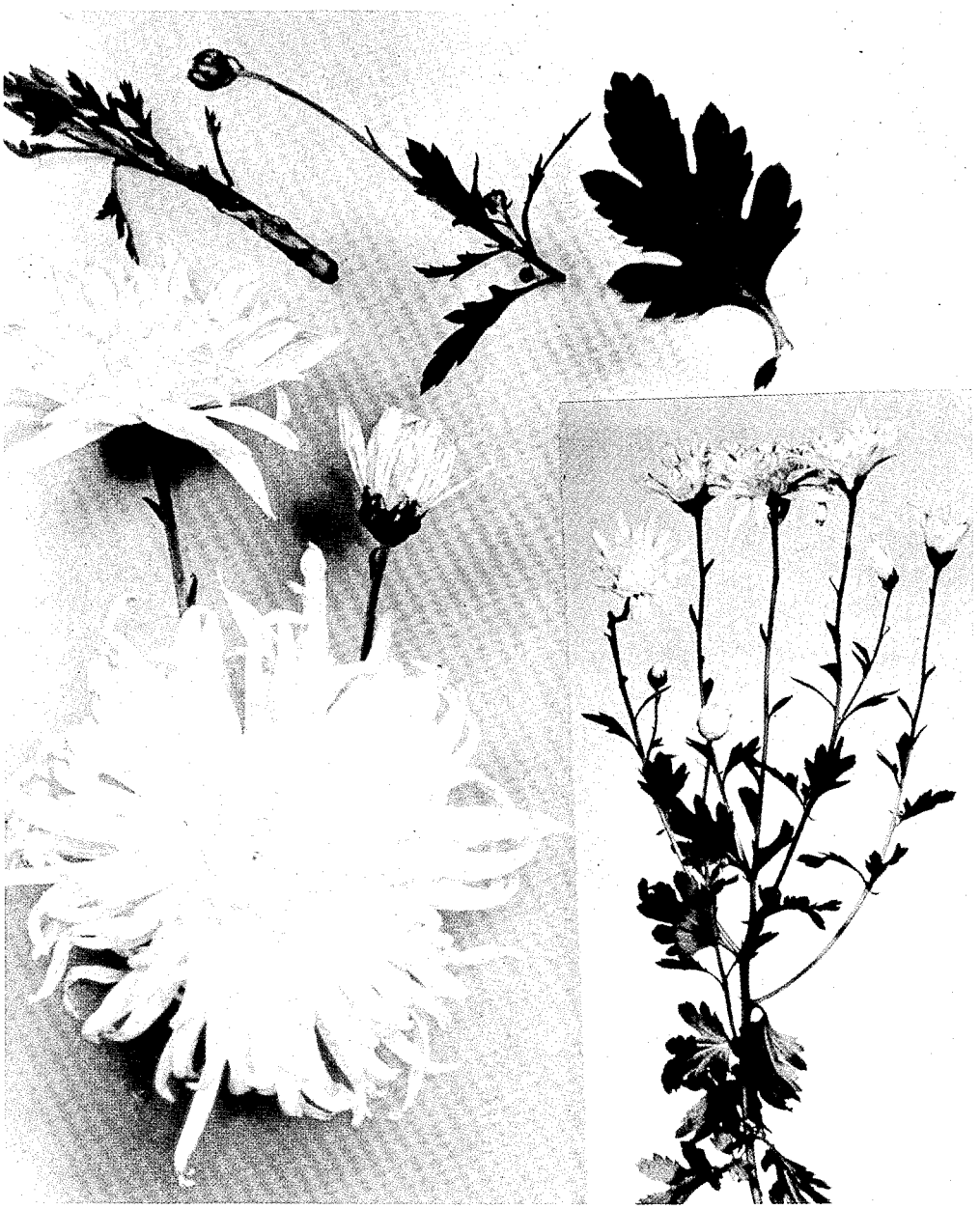
Inventor.
E. S. Boerner
By: Robb & Robb
Attorneys.

United States Patent Office

Plant Pat. 1,666
Patented Dec. 10, 1957

1,666

CHRYSANTHEMUM PLANT

Eugene S. Boerner, Newark, N. Y., assignor to Jackson & Perkins Company, Newark, N. Y., a corporation of New York Application April 12, 1957, Serial No. 652,638

1 Claim. (Cl. 47—60)

The present invention relates to a new and distinct variety of chrysanthemum plant of the decorative type, which was originated by me by crossing the variety "Yellow Seagull" (Plant Patent No. 1,547) with an unnamed and unpatented seedling derived from a cross of the variety "Thrush" (Plant Patent No. 1,168) × "Seagull" (Plant Patent No. 1,130).

The primary objective of this breeding was to produce a new chrysanthemum variety having a plant strength and vigor corresponding to that of the variety "Thrush," but which bears large White flowers. This objective was fully achieved, along with other improved features, as evidenced by the following characteristics which are outstanding in the new variety and which represent a unique combination in a chrysanthemum of this class:

(1) A strong and vigorous habit of plant growth;
(2) The wide form of the plant;
(3) The large size of the flowers;
(4) The shaggy flower petals; and
(5) The distinctive White general color tonality of the flowers.

The foregoing characteristics and distinctions definitely differentiate the new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flows of my new variety in different stages of development and as depicted in color as nearly true as it is reasonably possible to make the same in a color illustration of this character, as well as a typical specimen plant which is depicted in black-and-white as illustrative of the form and habit of growth of the plant.

The following is a detailed description of my new variety, with color terminology in accordance with Ridgway's Color Standards and Nomenclature, as based upon observations made from specimens grown outdoors at Newark, New York, in the late morning during the latter part of the month of September:

Parentage: "Yellow Seagull" × an unnamed seedling of "Thrush" × "Seagull."
Classification: Decorative.
Growth: Upright; attains a height averaging about 30 inches.
Cold resistance: Plants are very winter hardy in northern New York and flowers are frost-resistant.
Blooming period: In the Newark, New York, climatic area, blooming begins about September 15th and continues until heavy frosts.

*Flower*

Bud:
*Color.*—When sepals first divide—Chartreuse Yellow, Plate 31. When petals begin to unfurl—Sea-Foam Yellow, Plate 31. When half-blown: inside of petals—Marguerite Yellow, Plate 30; outside of petals—Sea-Foam Yellow, Plate 31.
*Peduncle.*—Strong. Color—Jade Green, Plate 31.

Bloom:
*Size.*—From 5½ to 6 inches.
*Stem.*—Thick; normal strength.
*Form.*—Decorative.
*Petalage.*—Very full; double; shaggy.
*Color.*—Center of flower—White, Plate 53, lightly overcast with Barium Yellow, Plate 4. Outer petals—White, Plate 53. Base of petals—Pale Greenish Yellow, Plate 5. Inside of petals—White, Plate 53. Reverse of petals—White, Plate 53.
*Petals.*—Texture—thick. Form—very long; wide; wavy.
*Fragrance.*—Characteristic chrysanthemum.

*Plant*

Form: Upright; wide.
Growth: Free; airy.
Foliage:
*Size.*—Medium.
*Quantity.*—Normal.
*Color.*—Upper side—Dark Dull Yellow Green, Plate 32. Reverse side—Light Hellebore Green, Plate 17.
*Texture.*—Leathery.

I claim:

A new and distinct variety of chrysanthemum plant of the decorative type, substantially as herein shown and described, characterized particularly as to novelty by its strong and vigorous habit of plant growth, the wide form of the plant, the large size of its flowers, the shaggy flower petals, and the distinctive White general color tonality of its flowers.

No references cited.